United States Patent

Marzolph et al.

Patent Number: 4,715,888
Date of Patent: Dec. 29, 1987

[54] HERBICIDAL AGENTS CONTAINING PHOTOSYNTHESIS-INHIBITING HERBICIDES IN COMBINATION WITH PYRIDINECARBOXAMIDES

[75] Inventors: Gerhard Marzolph, Cologne; Winfried Lunkenheimer, Wuppertal; Carl Fedtke, Cologne, all of Fed. Rep. of Germany

[73] Assignee: Bayer Aktiengesellschaft, Leverkusen, Fed. Rep. of Germany

[21] Appl. No.: 642,976

[22] Filed: Aug. 21, 1984

[30] Foreign Application Priority Data

Sep. 7, 1983 [DE] Fed. Rep. of Germany ....... 3332272

[51] Int. Cl.$^4$ ..................... A01N 43/64; A01N 43/40
[52] U.S. Cl. ............................................. 71/93; 71/94
[58] Field of Search ..................................... 71/93, 94

[56] References Cited

U.S. PATENT DOCUMENTS 3,450,706  6/1969  Wendler et al.
4,427,440  1/1984  von der Osten .......................... 71/94

FOREIGN PATENT DOCUMENTS 2616481  11/1977  Fed. Rep. of Germany.

OTHER PUBLICATIONS

Chemica Scripta, vol. 13, 1978–1979, p. 47.

Bulletin of the Ehcmical Society of Japan, vol. 44, 1971, pp. 1121–1125.
J. Chem. Soc. (C), 1967, pp. 1558–1567.
Carl Fedtke, Biochemistry and Physiology of Herbicide Action, 1982, Springer–Verlag, entire publication.

Primary Examiner—Catherine L. Mills
Attorney, Agent, or Firm—Sprung Horn Kramer & Woods

[57] ABSTRACT

The new synergistic active compound combinations consisting of (1) a photosynthesis-inhibiting active compound (herbicide) and (2) a pyridinecarboxamide of the general formula (synergistic agent)

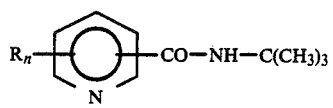

in which R represents alkyl, halogen, nitro, cyano, alkoxy, optionally substituted phenyl or optionally substituted benzyloxy, and the index n represents the numbers 0, 1, 2 or 3, have a particularly high herbicidal activity. Representative examples of the photosynthesis-inhibiting active compounds are metribuzin, ametridione, methabenzthiazuron, linuron, lenacil, atrazine and 4-amino-6-tert.-butyl-3-ethylthio-1,2,4-triazine-5-one.

9 Claims, No Drawings

HERBICIDAL AGENTS CONTAINING PHOTOSYNTHESIS-INHIBITING HERBICIDES IN COMBINATION WITH PYRIDINECARBOXAMIDES

The present invention relates to new herbicidal synergistic active compound combinations which consist, on the one hand, of known photosynthesis-inhibiting herbicides and, on the other hand, of certain pyridinecarboxamides, which are substantially known.

It has already been disclosed that certain herbicides, such as, for example, 4-amino-6-tert.-butyl-3-methylthio or -ethylthio-1,2,4-triazin-5-one; 1-amino-3-(2,2-dimethylpropyl)-6-(ethylthio)-1,3,5-triazine-2,4-dione; 6-chloro-2-ethylamino-4-isopropylamino-1,3,5-triazine; 1-methoxy-1-methyl-3-(3,4-dichlorophenyl)-urea; 1,3-dimethyl-1-(benzo-1,3-thiazol-2-yl)-urea or 3-cyclohexyl-5,6-trimethyleneuracil, possess photosynthesis-inhibiting properties (see, for example, Carl Fedtke, Biochemistry and Physiology of Herbicide Action, Springer Verlag, 1982). However, the disadvantage of these herbicidal compounds is that they do not always completely combat all weeds and graminaceous weeds which occur, or that, when applied, some species of crop plants are partially damaged.

It has been found that the new active compound combinations consisting of (a) a photosynthesis-inhibiting active compound (herbicide) and (b) a pyridinecarboxamide of the general formula (II) (synergistic agent)

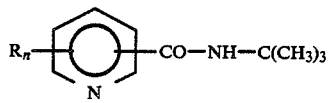

in which R repesents alkyl, halogen, nitro, cyano, alkoxy, optionally substituted phenyl or optionally substituted benzyloxy and the index n represents the numbers 0, 1, 2 or 3, have a particularly high herbicidal activity.

Surprisingly, the herbicidal activity of the active compound combinations according to the invention is substantially higher than the sum of the actions of the individual active compounds. In particular, the pyridinecarboxamides of the general formula (II), which are substantially known, do not themselves possess any herbicidal action when the customary amounts are applied, but result in an increase in the herbicidal action of the photosynthesis-inhibiting active compounds. Thus, the synergistic effect found here is completely unexpected and surprising.

Since the synergistic effect also relates to those weeds which are only insufficiently damaged or not combated at all when the photosynthesis-inhibiting active compounds are applied alone in customary amounts, the synergistic active compound combinations according to the invention represent a valuable enrichment of the art.

The following photosynthesis-inhibiting active compounds of the general formulae (I-A) to (I-J) may be preferably mentioned as photosynthesis-inhibiting active compounds for the active compound combinations according to the invention:

(A) Triazinone derivatives of the formula

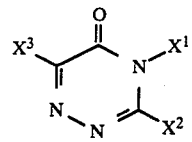

in which $X^1$ represents amino, optionally substituted alkylideneamino or alkyl having 1 or 2 carbon atoms;

$X^2$ represents alkylthio having 1 or 2 carbon atoms, alkyl- and dialkylamino, each having 1 or 2 carbon atoms in each alkyl part, or alkyl having 1 to 4 carbon atoms; and $X^3$ represents optionally halogen-substituted tert.-butyl or optionally substituted phenyl;

(B) Triazinedione derivatives of the formula

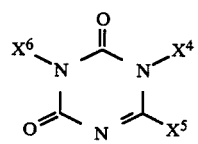

in which $X^4$ represents amino, optionally substituted alkylideneamino or alkyl having 1 or 2 carbon atoms;

$X^5$ represents alkylthio having 1 or 2 carbon atoms, alkyl- and dialkylamino, each having 1 or 2 carbon atoms in each alkyl part or alkyl having 1 to 4 carbon atoms; and $X^6$ represents alkyl having 1 to 6 carbon atoms or optionally substituted phenyl;

(c) Triazine derivatives of the formula

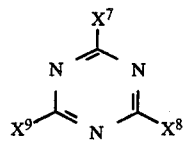

in which $X^7$ represents chlorine, alkoxy or alkylthio, each having 1 or 2 carbon atoms;

$X^8$ represents alkylamino having 1 to 4 carbon atoms in the alkyl part; and $X^9$ represents alkyl which has 1 to 4 carbon atoms and is optionally substituted by cyano;

(D) Urea derivatives of the formula

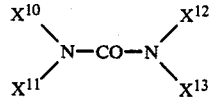

in which $X^{10}$ represents optionally substituted phenyl, benzothiazolyl or optionally substituted thiadiazolyl;

$X^{11}$ represents hydrogen or methyl;

$X^{12}$ represents methyl; and $X^{13}$ represents hydrogen, alkyl having 1 to 4 carbon atoms, alkoxy having 1 or 2 carbon atoms or alkinyl having 2 to 4 carbon atoms;

(E) Carboxanilide derivatives of the formula

 (I-E)

in which
X$^{14}$ represents alkyl having up to 6 carbon atoms, alkoxy having 1 to 4 carbon atoms, alkenyl having 2 to 4 carbon atoms or cycloalkyl having 3 to 6 carbon atoms; and
X$^{15}$ represents optionally substituted phenyl;

(F) Uracil derivatives of the formula

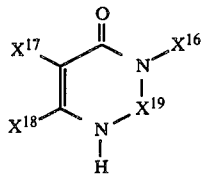 (I-F)

in which
X$^{16}$ represents alkyl having 1 to 6 carbon atoms or cycloalkyl having 5 to 7 carbon atoms;
X$^{17}$ represents halogen;
X$^{18}$ represents alkyl having 1 or 2 carbon atoms, or
X$^{17}$ and X$^{18}$ together represent an optionally substituted alkylene chain or an optionally substituted fused benzene ring; and
X$^{19}$ represents the —CO— or —SO$_2$— group;

(G) Biscarbamate derivatives of the formula

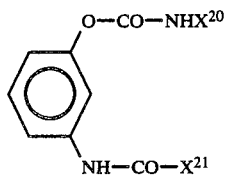 (I-G)

in which
X$^{20}$ represents alkyl having 1 to 4 carbon atoms or optionally substituted phenyl; and
X$^{21}$ represents alkoxy having 1 to 4 carbon atoms or dialkylamino having 1 or 2 carbon atoms in each alkyl part;

(H) Pyridazinone derivatives of the formula

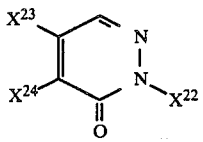 (I-H)

in which
X$^{22}$ represents optionally substituted phenyl;
X$^{23}$ represents amino, alkylamino or dialkylamino, each having 1 or 2 carbon atoms in each alkyl part; and
X$^{24}$ represents halogen;

(J) Hydroxybenzonitrile derivatives of the formula

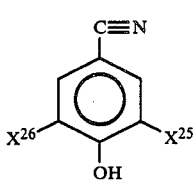 (I-J)

in which
X$^{25}$ represents halogen; and
X$^{26}$ represents halogen.

Particularly preferred photosynthesis-inhibiting active compounds are those of the general formulae (I-A) to (I-J):

(A) Triazinone derivatives of the formula

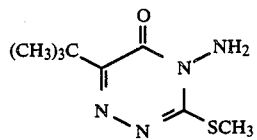 (I-A-1)

(metribuzin)

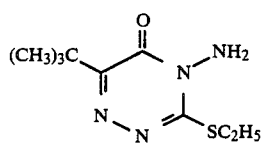 (I-A-2)

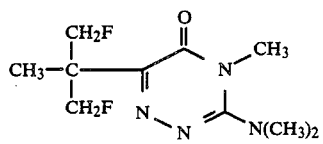 (I-A-3)

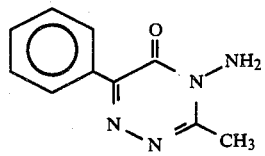 (I-A-4)

(metamitron)

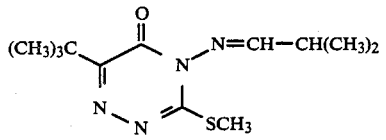 (I-A-5)

(isomethiozin)

(B) A triazinedione derivative of the formula

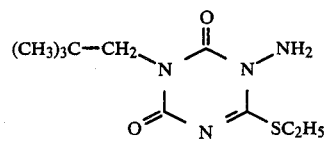 (I-B-1)

(ametridione)

(C) Triazine derivatives of the formula

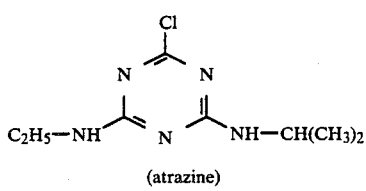 (I-C-1)

(atrazine)

-continued
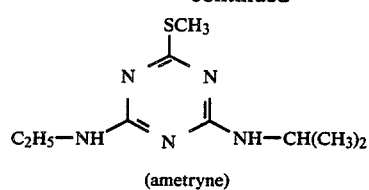
(ametryne) (I-C-2)
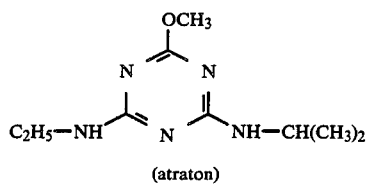
(atraton) (I-C-3)
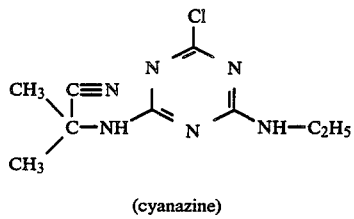
(cyanazine) (I-C-4)
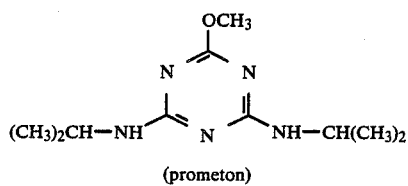
(prometon) (I-C-5)
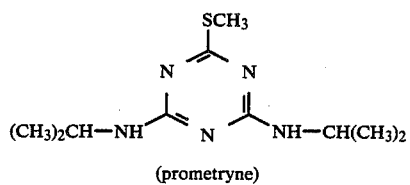
(prometryne) (I-C-6)
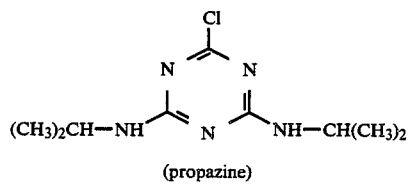
(propazine) (I-C-7)
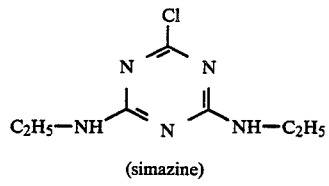
(simazine) (I-C-8)
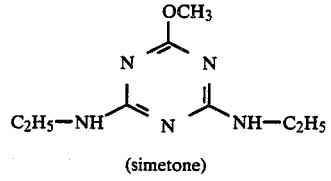
(simetone) (I-C-9)
-continued
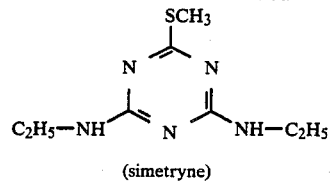
(simetryne) (I-C-10)
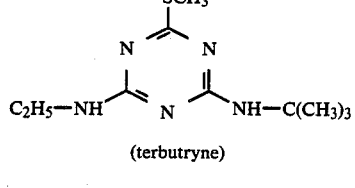
(terbutryne) (I-C-11)
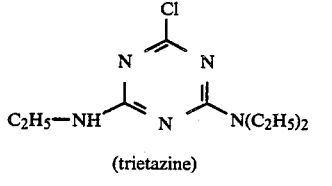
(trietazine) (I-C-12)
(D) Urea derivatives of the formulae
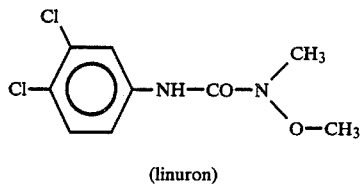
(linuron) (I-D-1)
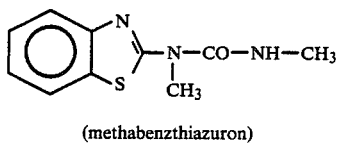
(methabenzthiazuron) (I-D-2)
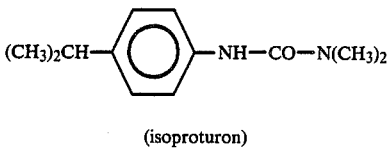
(isoproturon) (I-D-3)
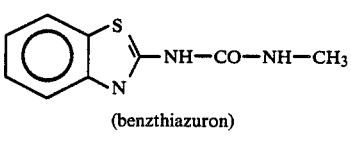
(benzthiazuron) (I-D-4)
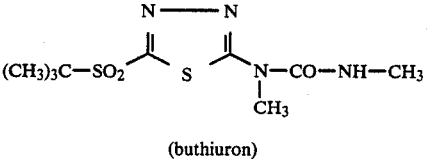
(buthiuron) (I-D-5)
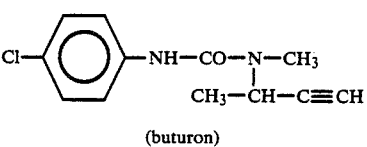
(buturon) (I-D-6)

-continued
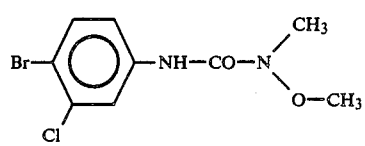
(chlorbromuron) (I-D-7)
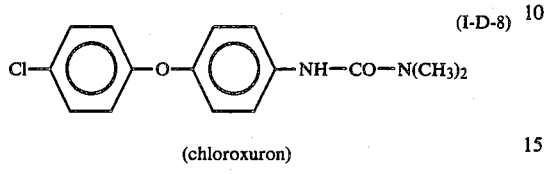
(chloroxuron) (I-D-8)
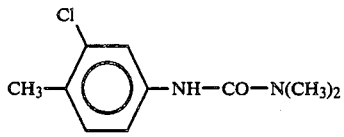
(chlortoluron) (I-D-9)
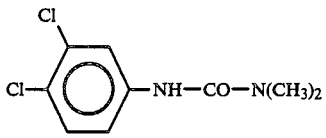
(diuron) (I-D-10)
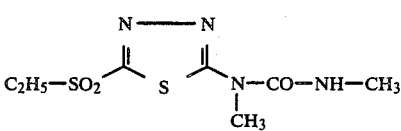
(ethidimuron) (I-D-11)
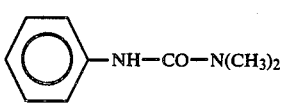
(fenuron) (I-D-12)
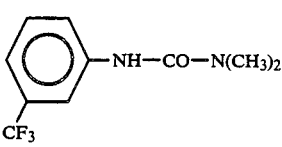
(fluometuron) (I-D-13)
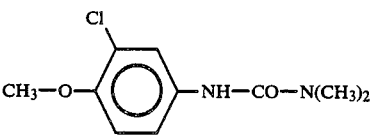
(metoxuron) (I-D-14)
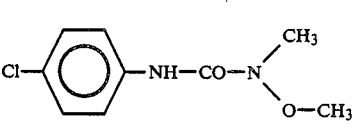
(monolinuron) (I-D-15)
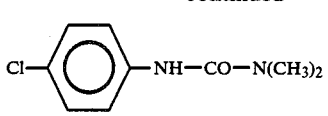
(monuron) (I-D-16)
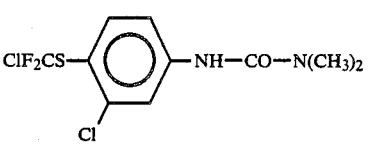
(neburon) (I-D-17)
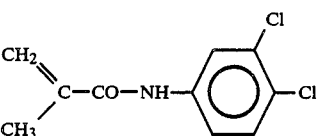
(tebuthiuron) (I-D-18)
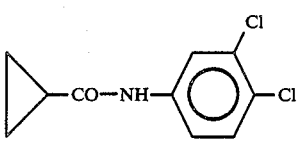
(thiochlormethyl) (I-D-19)
(E) Carboxanilide derivatives of the formula
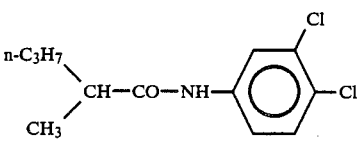
(chlorancryl) (I-E-1)
(I-E-2)
(cypromid)
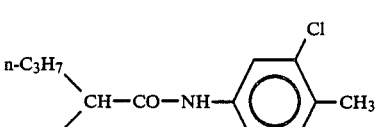
(Karsil) (I-E-3)
(I-E-4)
(pentanochlor)

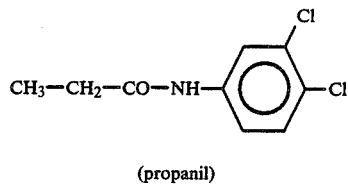
(propanil)
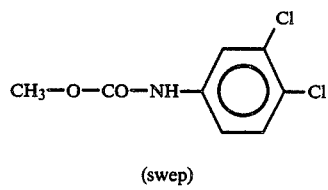
(swep)
(F) Uracil derivatives of the formula
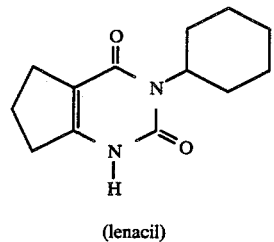
(lenacil)
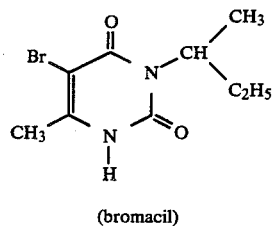
(bromacil)
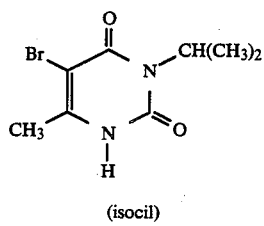
(isocil)
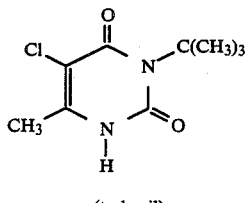
(terbacil)
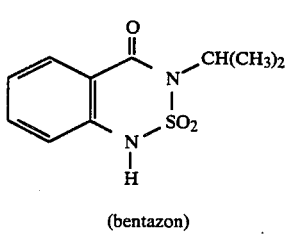
(bentazon)
(G) Biscarbamate derivatives of the formula
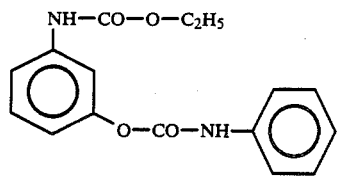
(desmedipham)
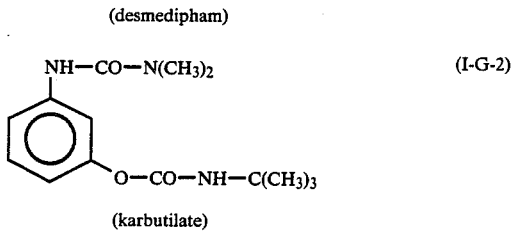
(karbutilate)
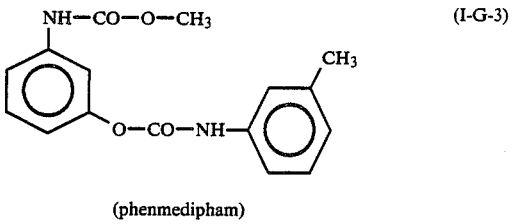
(phenmedipham)
(H) Pyridazinone derivatives of the formula
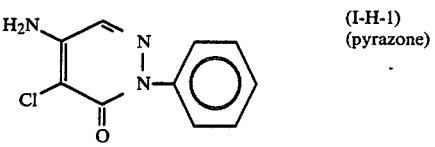
(pyrazone)
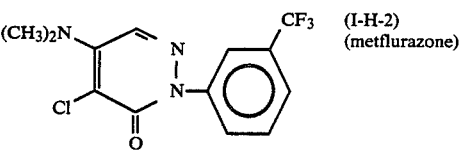
(metflurazone)
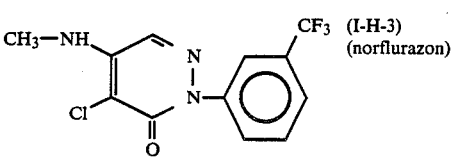
(norflurazon)
(J) Hydroxybenzonitrile derivatives of the formula
(bromoxynil)
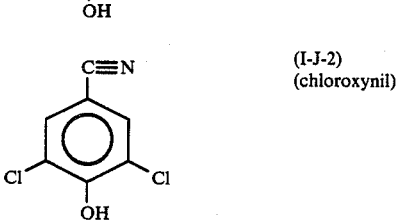
(chloroxynil)

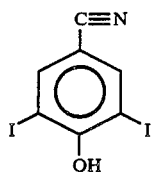
(I-J-3)
(ioxynil)

The photosynthesis-inhibiting active compounds of the formulae (I-A) to (I-J) are known (see, for example, Carl Fedtke, Biochemistry and Physiology of Herbicide Action, Springer Verlag, 1982).

Formula (II) gives a general definition of the pyridinecarboxamides furthermore to be used as components of the mixture. In this formula, R preferably represents straight-chain or branched alkyl having 1 to 6 carbon atoms, fluorine, chlorine, bromine, nitro, cyano and alkoxy having 1 to 8 carbon atoms, and phenyl and benzyloxy, each of which is optionally monosubstituted to trisubstituted by identical or different substituents, the following being mentioned as substituents in the phenyl part in each case: halogen, alkyl having 1 to 4 carbon atoms, alkoxy having 1 or 2 carbon atoms, nitro and cyano; and the index n preferably represents the numbers 0, 1, 2 and 3. Particularly preferred compounds of the formula (II) are those in which R represents methyl, ethyl, chlorine, nitro, cyano and methoxy, and phenyl or benzyloxy, each of which is optionally monosubstituted or disubstituted by chlorine and/or methyl, and the index n represents the numbers 0, 1 or 2.

Pyridinecarboxamides of the formula (II) are known (see, for example, Chemica Scripta 13, (1978–79), page 47; Bulletin of the Chemical Society of Japan 44, (1971), pages 1121–1125; J. Chem. Soc. (D) 1967, pages 1558–1564; U.S. Pat. No. 3,450,706 and DE-OS (German Published Specification) No. 2,616,481); they can be obtained in a customary manner, such as, for example, by reacting the corresponding cyanopyridines with appropriate alcohols in the presence of a strong acid (also see preparation examples).

The weight ratios of the active compound groups in the new active compound combinations can vary within relatively wide ranges. In general, 0.25 to 100, preferably 5 to 50, in particular 10 to 20, parts by weight of the pyridinecarboxamide of the formula (II) (synergistic agent) are employed per part by weight of the photosynthesis-inhibiting active compound (herbicidal active compound).

The photosynthesis-inhibiting active compounds have powerful herbicidal actions. In spite of this, their action against some weeds, such as, for example, *Galium aparine, Ipomoea hederacea, Datura stramonium, Cirsium arrense, Convolvulus arvensis* or *Solanum nigrum*, and some graminaceous weeds, such as, for example, *Agropyron repens, Avena fatua, Cynodon dactylon,* Cyperus ssp. and *Colium rigidum*, is not always adequate. The active compound combinations according to the invention extend the action spectrum of the compounds of the formulae (I-A to I-J) and hence make it possible to combat these weeds, which can be combated only with difficulty, it at all, with the photosynthesis-inhibiting herbicides alone.

The active compound combinations according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compound conbinations according to the invention is in no way restricted to these genera, but also extends in the same manner to other plants.

The active compound combinations according to the invention exhibit a good action against graminaceous weeds as well as, in particular, a good herbicidal action in the case of broad-leaved weeds.

The active compound combinations according to the invention can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is, liquid solvents and/or solid carriers, optionally with the use of surface-active agents, that is, emulsifying agents and/or dispersing agents, and/or foaming-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes of methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example nonionic and anionic emusifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolys products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol or polyvinyl acetate, can be used in the formulations.

In the formulations, it is possible to use, as further additives, colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound combination, preferably between 0.5 and 90%.

The active compound combinations according to the invention are brought into use in general in the form of finished formulations. However, the active compounds present in the active compound combinations can also be mixed, as individual formulations, during use, that is to say they can be brought into use in the form of tank mixtures.

The new active compound combinations, as such or in the form of their formulations, can also be used as mixtures with other known herbicides, finished formulations or tank mixtures once again being possible. Mixtures with other known active compounds, such as fungicides, insecticides, acaricides, nematicides, bird repellents, growth factors, plant nutrients and agents which improve the soil structure, are also possible.

The new active compound combinations can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, dusting or scattering.

The active compound combinations according to the invention can be applied either before or after sowing as well as after emergence of the plants, joint or separate application being possible. In this context, the sequence of application is unimportant.

When the synergistic agents according to the invention are used, the amount of the herbicide of the formulae (I-A to I-J) which is customarily applied can be reduced. In the case of treatment of an area, the amount of herbicidal photosynthesis-inhibiting active compound applied is between 0.01 and 3.0 kg/ha, preferably between 0.05 and 2.0 kg/ha.

In the case of the treatment of an area, the amount of synergistic pyridinecarboxamide applied is between 0.1 and 10 kg/ha, preferably between 0.5 and 3 kg/ha.

The good herbicidal action of the active compound combinations according to the invention can be seen from the examples which follow. While the individual active compounds have weaknesses in the herbicidal action, the combinations show an action against weeds which goes beyond a simple additive action.

A synergistic effect is present in herbicides whenever the herbicidal action of the active compound combination is greater than the sum of the actions of the active compounds applied.

EXAMPLE A

Pre-emergence test

Solvent: 5 parts by weight of acetone
Emulsifier: 1 part by weight of alkylaryl polyglycol ether To produce a suitable preparation of active compound, 1 part by weight of the herbicidal active compound or the synergistic agent, or of a mixture of the herbicidal active compound and the synergistic agent, is mixed with the stated amount of solvent, the stated amount of emulsifier is added and the concentrate is diluted with water to the desired concentration.

Seeds of the test plants are sown in normal soil and, after 24 hours, watered with a preparation of the herbicide or with the preparation of the synergistic agent or with the preparation of the synergistic agent and the herbicidal active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control.

The figures denote:
0% = no action (like untreated control)
100% = total destruction Active compounds, amount applied and results can be seen in the Tables below.

Pre-emergence test

TABLE A₁

Synergistic action of pyridinecarboxamides (II) (= synergistic agent S) and 4-amino-6-tert.-butyl-3-methylthio-1,2,4-triazin-5-one (I-A-1) (= herbicide H) on *Ipomoea hederacea*. The amount applied in kg/ha is relatvie to the content of active compound.

| Structure of the synergistic agent | (S) kg/ha | (H) kg/ha | % damage in the case of *Ipomoea hederacea* | | |
|---|---|---|---|---|---|
| | | | H | S | H + S |
| 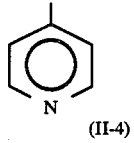 (II-4) | 0.5 | 0.05 | 0 | 0 | 0 |
| | 2 | 0.05 | 0 | 0 | 0 |
| | 0.5 | 0.15 | 0 | 0 | 20 |
| | 2 | 0.15 | 0 | 0 | 20 |

TABLE A1-continued

Synergistic action of pyridinecarboxamides (II)
(= synergistic agent S) and 4-amino-6-tert.-butyl-3-
methylthio-1,2,4-triazin-5-one (I-A-1) (= herbicide H)
on *Ipomoea hederacea*. The amount applied in kg/ha is
relatvie to the content of active compound.

| Structure of the synergistic agent | (S) kg/ha | (H) kg/ha | H | S | H + S |
|---|---|---|---|---|---|
| 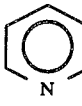<br>(II-2) | 0.5<br>2<br>0.5<br>2 | 0.05<br>0.05<br>0.15<br>0.15 | 0<br>0<br>20<br>20 | 0<br>0<br>0<br>0 | 80<br>80<br>100<br>100 |
| 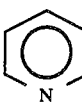<br>(II-3) | 0.5<br>2<br>0.5<br>2 | 0.05<br>0.05<br>0.15<br>0.15 | 0<br>0<br>40<br>40 | 0<br>0<br>0<br>0 | 10<br>70<br>50<br>100 |
| 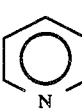<br>(II-1) | 0.5<br>2<br>0.5<br>2 | 0.05<br>0.05<br>0.15<br>0.15 | 0<br>0<br>30<br>30 | 0<br>0<br>0<br>0 | 90<br>100<br>100<br>100 |
| 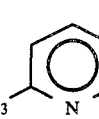<br>(II-5) | 0.5<br>2<br>0.5<br>2 | 0.05<br>0.05<br>0.15<br>0.15 | 10<br>10<br>20<br>20 | 0<br>0<br>0<br>0 | 80<br>90<br>100<br>100 |
| 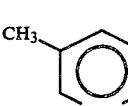<br>(II-6) | 0.5<br>2<br>0.5<br>2 | 0.05<br>0.05<br>0.15<br>0.15 | 10<br>10<br>20<br>20 | 0<br>0<br>0<br>0 | 40<br>40<br>40<br>100 |
| 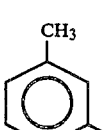<br>(II-7) | 0.03<br>0.1<br>0.3<br>1<br>2 | 0.1<br>0.1<br>0.1<br>0.1<br>0.1 | 20<br>20<br>20<br>20<br>20 | <br><br><br><br>0 | 10<br>20<br>20<br>40<br>100 |
| <br>(II-8) | 0.03<br>0.1<br>0.3<br>1<br>2 | 0.1<br>0.1<br>0.1<br>0.1<br>0.1 | 40<br>40<br>40<br>40<br>40 | <br><br><br><br>10 | 90<br>80<br>90<br>100<br>100 |
| <br>(II-9) | 0.03<br>0.1<br>0.3<br>1<br>2 | 0.1<br>0.1<br>0.1<br>0.1<br>0.1 | 40<br>40<br>40<br>40<br>40 | <br><br><br><br>0 | 20<br>30<br>40<br>100<br>100 |
| 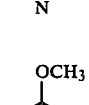<br>(II-10) | 0.03<br>0.1<br>0.3<br>1<br>2 | 0.1<br>0.1<br>0.1<br>0.1<br>0.1 | 10<br>10<br>10<br>10<br>10 | <br><br><br><br>0 | 10<br>20<br>30<br>40<br>60 |
| 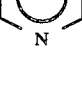 | 0.03<br>0.1<br>0.3<br>1<br>2 | 0.1<br>0.1<br>0.1<br>0.1<br>0.1 | 0<br>0<br>0<br>0<br>0 | <br><br><br><br>20 | 20<br>30<br>30<br>100<br>100 |

TABLE A₁-continued

Synergistic action of pyridinecarboxamides (II) (= synergistic agent S) and 4-amino-6-tert.-butyl-3-methylthio-1,2,4-triazin-5-one (I-A-1) (= herbicide H) on *Ipomoea hederacea*. The amount applied in kg/ha is relatvie to the content of active compound.

| Structure of the synergistic agent | (S) kg/ha | (H) kg/ha | % damage in the case of *Ipomoea hederacea* | | |
|---|---|---|---|---|---|
| | | | H | S | H + S |
| (II-11) | | | | | |

The use of the herbicide (I-A-1) alone in a concentration of 0.5 and 2.0 kg/ha results in, respectively, 80 and 95% damage in the case of Ipomoea hederacea.

TABLE A₂

Synergistic action of the pyridinecarboxamide according to Preparation Example (II-2) and various photosynthesis-inhibiting herbicides on Ipomoea hederacea. The amount applied in kg/ha is relative to the content of active compound.

| | | Synergistic agent | | |
|---|---|---|---|---|
| | Preparation Example (II-2) kg/ha | 0 kg/ha | 0.5 kg/ha | 2.0 kg/ha |
| Herbicide | | % action in the case of Ipomoea hederacea | | |
| metribuzin | 0.05 | 30 | 60 | 80 |
| (I-A-1) | 0.07 | 30 | 80 | 100 |
| | 0.1 | 40 | 90 | 90 |
| ametridione | 0.5 | 50 | 100 | 90 |
| (I-B-1) | | | | |
| (I-A-2) | 0.3 | 0 | 100 | 60 |
| | 1.0 | 20 | 100 | 100 |
| methabenzthiazuron | 3.0 | 40 | 100 | 100 |
| (I-D-2) | | | | |
| linuron | 0.5 | 20 | 50 | 50 |
| (I-D-1) | 1.0 | 60 | 80 | 90 |
| lenacil | 3.0 | 10 | 40 | 90 |
| (I-F-1) | | | | |
| Herbicide | 0 | 0 | 0 | 0 |

TABLE A₃

Synergistic action of the pyridinecarboxamide according to Preparation Example (II-2) and various photosynthesis-inhibiting herbicides on Ipomoea hederacea. Synergistic agent: Preparation Example (II-2); mixing ratio herbicide (H): synergistic agent (S) = 1:4 Test plant: Ipomoea hederacea

| | Herbicide without synergistic agent | | Herbicide + synergistic agent | |
|---|---|---|---|---|
| Treatment | kg/ha H | action in % | kg/ha H + S | action in % |
| metribuzin ± (II-2) (I-A-1) | 0.1 | 3 | 0.1 + 0.4 | 100 |
| ametridione ± (II-2) (I-B-1) | 0.2 | 1 | 0.2 + 0.8 | 63 |
| atrazine ± (II-2) (I-C-1) | 0.025 | 16 | 0.025 + 0.1 | 33 |
| linuron ± (II-2) (I-D-1) | 0.1 | 14 | 0.1 + 0.4 | 95 |
| — (II-2) | — | — | 0.0 + 0.8 | 15 |

PREPARATION EXAMPLES

Example 1

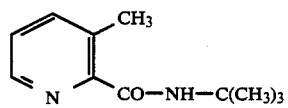

(II-1)

111 g (1.5 mol) of tert.-butanol and 118 g (1 mol) of 3-methyl-2-cyanopyridine in 100 ml of glacial acetic acid are initially taken. 147 g of sulphuric acid (100% strength) are added dropwise to this mixture at 50° C. in the course of 0.5 hours, and the mixture is stirred for 3 hours at 50° C. The oil is stirred into 1,000 ml of water, and the resulting solution is adjusted to pH 7 with concentrated sodium hydroxide solution, while cooling with ice. The oil which separates out is separated off, taken up in methylene chloride and extracted by shaking with water. The organic phase is dried over sodium sulphate, evaporated down and distilled. 166.5 g (86.7% of theory) of 3-methylpyridine-2-carboxylic acid N-tert.-butylamide are obtained as a viscous oil of boiling point 155° C./4 mbar.

The compounds of the general formula (II)

$$R_n\text{—pyridine—}CO\text{—}NH\text{—}C(CH_3)_3 \quad (II)$$

can be obtained in an analogous manner (see Table 1):

TABLE 1

| Example No. | Structure | Physical constant |
|---|---|---|
| (II-2) | pyridine-CO—NH—C(CH₃)₃ | B.p.: 175° C./ 20 mbar |
| (II-3) | pyridine-CO—NH—C(CH₃)₃ | M.p.: 79–82° C. |
| (II-4) | pyridine-CO—NH—C(CH₃)₃ | M.p.: 119–23° C. |
| (II-5) | CH₃-pyridine-CO—NH—C(CH₃)₃ | viscous oil |
| (II-6) | CH₃-pyridine-CO—NH—C(CH₃)₃ | M.p.: 107–08° C. |

TABLE 1-continued

| Example No. | Structure | Physical constant |
|---|---|---|
| (II-7) | 4-methyl-pyridine-2-CO—NH—C(CH₃)₃ | viscous oil |
| (II-8) | 3-chloro-pyridine-2-CO—NH—C(CH₃)₃ | M.p.: 103–06° C. |
| (II-6) | 3-ethyl-pyridine-2-CO—NH—C(CH₃)₃ | viscous oil |
| (II-10) | 4-methoxy-pyridine-2-CO—NH—C(CH₃)₃ | viscous oil |
| (II-11) | 6-methoxy-pyridine-2-CO—NH—C(CH₃)₃ | viscous oil |

It will be understood that the specification and examples are illustrative but not limitative of the present invention and that other embodiments within the spirit and scope of the invention will suggest themselves to those skilled in the art.

What is claimed is:

1. A herbicidal composition consisting essentially of a herbicidally effective and selective amount of
   (a) a photosynthesis-inhibiting active compound (herbicide) plus
   (b) 0.25 to 100 times its weight of pyridine-2-carboxylic acid N-tert.-butylamide.

2. A composition according to claim 1, wherein (a) is 4-amino-6-tert.-butyl-3-methylthio-1,2,4-triazin-5-one (metribuzin) of the formula

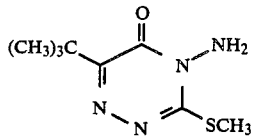

3. A composition according to claim 1, wherein the weight ratio of (a):(b) is from about 1:5 to 1:50.

4. A composition according to claim 1, wherein the weight ratio of (a):(b) is from about 1:10 to 1:20.

5. A method of combating unwanted vegetation which comprises applying to such vegetation or to a field from which it is desired to exclude such vegetation a herbicidally effective amount of a composition according to claim 1.

6. A method of combating unwanted vegetation which comprises applying to such vegetation or to a field from which it is desired to exclude such vegetation a herbicidally effective amount of a composition according to claim 1.

7. In combating of unwanted vegetation by applying a photosynthesis-inhibiting herbicide to such vegetation or to a field from which it is desired to exclude such vegetation, the improvement which comprises also applying to such field a herbicidally and synergistically effective amount of pyridine-2-carboxyliacid N-tert.-butylamide, in 0.25 to 100 times the weight of the herbicide.

8. The method according to claim 7 wherein the herbicide is metribuzin.

9. The method according to claim 8 wherein the herbicide and synergist are applied to a field in which soy beans are growing or are to be grown.

* * * * *

UNITED STATES PATENT AND TRADEMARK OFFICE
CERTIFICATE OF CORRECTION

PATENT NO. : 4,715,888

DATED : December 29, 1987

INVENTOR(S) : Gerhard Marzolph, et al.

It is certified that error appears in the above-identified patent and that said Letters Patent is hereby corrected as shown below:

| | |
|---|---|
| Title Page, under "U.S. Patent Documents", line 2 | After "von der Osten" insert --et al-- |
| Col. 11, line 37 | Before "1967" delete (D)" and substitute --(C)-- |
| Col. 12, lines 23-24 | Correct spelling of --combinations-- |
| Col. 14, line 59, 5th line under Table $A_1$; Col. 15, line 6; Col. 17, line 6 | Correct spelling of --relative-- |
| Col. 19, line 18 | Delete "(II-6)" and substitute --(II-9)-- |
| Col. 20, line 35 | Delete "carboxyliacid" and substitute --carboxylic acid-- |

Signed and Sealed this

Thirtieth Day of August, 1988

Attest:

DONALD J. QUIGG

Attesting Officer     Commissioner of Patents and Trademarks